United States Patent [19]

Aichinger et al.

[11] Patent Number: 5,767,306
[45] Date of Patent: Jun. 16, 1998

[54] ESTERIFICATION OF (METH)ACRYLIC ACID WITH AN ALKANOL

[75] Inventors: Heinrich Aichinger, Mannheim; Michael Fried, Heidelberg; Gerhard Nestler, Ludwigshafen, all of Germany

[73] Assignee: BASF Aktiengesellschaft, Ludwigshafen, Germany

[21] Appl. No.: 701,990

[22] Filed: Aug. 23, 1996

[30] Foreign Application Priority Data

Sep. 28, 1995 [DE] Germany ............ 195 36 184.9

[51] Int. Cl.[6] .................................. C07C 67/30
[52] U.S. Cl. ........................... 560/212; 560/218
[58] Field of Search ............................. 560/218, 212

[56] References Cited

U.S. PATENT DOCUMENTS 3,261,767  7/1966  Knärr et al. .................... 560/218

FOREIGN PATENT DOCUMENTS

| | | |
|---|---|---|
| 1 058 390 | 2/1992 | China . |
| 1 063 678 | 8/1992 | China . |
| 2 339 519 | 2/1974 | Germany . |
| 195 47 485 | 5/1996 | Germany . |
| 47-15936 | 5/1972 | Japan . |
| 57-62229 | 4/1982 | Japan . |
| 5-25086 | 2/1993 | Japan . |
| 6-65149 | 3/1994 | Japan . |
| 923 595 | 4/1963 | United Kingdom . |

*Primary Examiner*—Paul J. Killos
*Attorney, Agent, or Firm*—Oblon, Spivak, McClelland, Maier & Neustadt, P.C.

[57] ABSTRACT

In a process for esterifying (meth)acrylic acid with an alkanol in the presence of an esterification catalyst, in which unconverted starting compounds and the (meth)acrylate to be formed are separated off by distillation and an oxyester-containing bottom product is formed, the bottom product is first separated off, the oxyesters contained therein are then separated off by distillation and the resulting distillate is cleaved in the presence of acids at elevated temperatures. The process can be carried out in the presence of molecular oxygen. The distillate is cleaved at from 170° to 250° C., preferably from 180° to 230° C.

11 Claims, No Drawings

ESTERIFICATION OF (METH)ACRYLIC ACID WITH AN ALKANOL

The present invention relates to a process for esterifying (meth)acrylic acid with an alkanol in the presence of an esterification catalyst, in which unconverted starting compounds and the (meth)acrylate to be formed are separated off by distillation, and an oxyester-containing bottom product is formed. The term (meth)acrylic acid denotes in a known manner acrylic or methacrylic acid.

Alkyl esters of (meth)acrylic acid are usually prepared by esterifying (meth)acrylic acid with alkanols at elevated temperatures in the liquid phase in the presence or absence of a solvent and in the presence of an acid as a catalyst (DE-A 23 39 519). The disadvantage of this method of preparation is that, as secondary reactions under the above-mentioned esterification conditions, unconverted starting alcohol undergoes a Michael addition reaction at the double bond of the resulting alkyl (meth)acrylate with formation of a compound of the general formula I below, and unconverted (meth)acrylic acid undergoes said addition reaction with formation of a compound of the general formula II. Multiple addition is also possible. Furthermore, mixed types may occur. These adducts (alkoxyesters and acyloxyesters) are referred to as oxyesters for short.

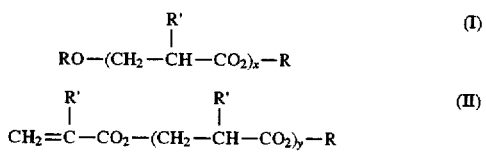

where x and y are each 1–5,
R is alkyl and
R' is H or $CH_3$

If R' is H, the esterification in question is that of acrylic acid; if R' is $CH_3$, the esterification in question is that of methacrylic acid.

In the preparation of esters of acrylic acid, the problem of oxyester formation is particularly acute, the oxyesters mainly formed being the alkoxypropionic esters and the acyloxypropionic esters where x and y are each 1. In the preparation of esters of methacrylic acid, the oxyester formation takes place to a lesser extent. The formation of oxyesters is described in DE-A 23 39 529. This states that the formation of oxyesters is essentially independent of the esterification conditions. Of very particular importance is the oxyester formation in the preparation of acrylates of $C_1$–$C_8$-alkanols, in particular of $C_4$–$C_8$-alkanols, very particularly in the preparation of n-butyl acrylate and 2-ethylhexyl acrylate.

Typical for the oxyesters is that their boiling point is above the boiling points of starting acid, starting alcohol, target ester formed and any organic solvent present.

Any desired esterification reaction mixture is usually worked up by separating unconverted starting compounds and the target ester from the reaction mixture by distillation, the acid catalyst used for the esterification being separated off beforehand, if required, by extraction by means of water and/or aqueous alkali (cf. for example Ullmann's Encylopedia of Industrial Chemistry, Vol. A1, 5th Ed. VCH, page 167 et seq.). The bottom product remaining as a result of such a working up by distillation contains the oxyesters, which give rise to considerable loss of yield.

Various other processes have therefore been investigated in order to solve the problems arising from the occurrence of the oxyesters. Thus, JP-A-82/62229 describes the alkaline hydrolysis of the high-boiling esterification residue. A part of the alcohol used and acrylic acid and β-hydroxypropionic acid or salts thereof are recovered in this manner. A simple and economical recycling of the products to the esterification reaction is therefore not possible. Japanese Published Application 72/15936 describes the preparation of acrylates by reacting β-alkoxypropionic esters with acrylic acid in the presence of strong acids (transesterification). However, equimolar amounts of β-alkoxypropionic acid are obtained as a byproduct and cannot be recycled to the esterification reaction and therefore constitute waste. JP-A-93/25086 describes the cleavage of the Michael adduct butyl β-butoxypropionate (cf. formula I, x=1, R=butyl) at elevated temperatures and in the presence of sulfuric acid and of an excess of water. However, the conversion is only about 30%. Finally, JP-A-94/65149 describes the cleavage of the Michael adducts I and II (see above, x=y=1) in the presence of titanium alcoholates. Here, the conversion is likewise low (<60%) and large amounts of titanate are required. This process is therefore uneconomical and, owing to the large amounts of titanate to be disposed of, causes environmental pollution.

GB 923 595 describes the recovery of monomers from the residue of the esterification of acrylic acid with alkanols in the absence of molecular oxygen. Inter alia, the removal of all volatile monomers prior to the cleavage, cleavage in the presence of sulfuric acid and the removal of the cleavage products with the aid of an inert gas stream are recommended. According to the Examples, the cleavage is always carried out at not less than 300° C. Coke is formed as a residue (17–40%). This has to be removed from the reactor by a procedure resembling mining. This process is therefore neither economical nor feasible on an industrial scale. A further disadvantage is the required exclusion of oxygen.

CN-A 1,063,678 describes the cleavage of the alkoxypropionic ester contained in the esterification residue, in the presence of sulfuric acid, in a cascade, the temperature and catalyst concentration (0.8–1.5%) differing in each reactor. Coupled to the cleavage is a distillation for the separation of alkanol and acrylate. The process is very inconvenient and does not give high conversions.

Finally, CN-A 105 8390 describes the cleavage of alkoxypropionic esters in the presence of sulfuric acid, etc. into alkanols and acrylates. This is a stepwise procedure. First, the cleavage is carried out under reflux and then the reaction products are distilled off. The cleavage of the acrylate-containing ester residues of the ethyl/methyl acrylate preparation (ethyl ethoxypropionate, methyl methoxypropionate) is carried out in the presence of ethanol and methanol, respectively. Here too, the process is complicated and does not give high conversions.

It is an object of the present invention to carry out the recleavage of the oxyesters contained in this bottom product and the further use of the resulting starting acid, starting alcohol and target ester in the esterification without the disadvantages of the prior art processes.

We have found that this object is achieved, according to the invention, if the bottom product is first separated off, the oxyesters contained therein are then separated off by distillation and the resulting distillate is cleaved in the presence of acids at elevated temperatures. The amount of the oxyesters distilled off is as a rule from 75 to 95% by weight of the bottom product. In an advantageous embodiment of the invention, the process is carried out in the presence of molecular oxygen.

It has also been proposed to carry out the recleavage of the oxyesters while they are present in the bottom product, but this procedure has the disadvantage that the highly viscous residue remaining after the end of the recleavage is difficult to dispose of. Surprisingly, the novel process does not have this disadvantage. Moreover, when the novel process is carried out by a semicontinuous procedure, an initially taken amount of acidic cleavage catalyst is capable of cleaving a larger amount of continuously introduced starting material than in the case of a cleavage carried out in the bottom product.

Both the residue remaining when the oxyesters are distilled off and the residue of the cleavage process have a low viscosity.

In an advantageous development of the invention, for example, mineral acids, such as sulfuric acid or phosphoric acid, and/or organic acids, such as alkanesulfonic or arylsulfonic acids, for example methanesulfonic or p-toluenesulfonic acid, are added to the distillate as acids. The total amount of acid then present is from 1 to 20, preferably from 5 to 15, % by weight, based on the amounts of the bottom product. It is particularly advantageous if, as an entraining agent for the cleavage products, a stripping gas which preferably contains molecular oxygen is passed through the bottom product. Air or a mixture of air with an inert gas (eg. nitrogen) is advantageously used as the stripping gas.

A simple heatable stirred reactor having a double-wall heating means or heating coil or a forced-circulation evaporator, for example a falling-film evaporator or flash evaporator, coupled to a dwell container, can be used for working up the oxyesters obtained as bottom product in the esterification. For better separation of the cleavage products, a rectification apparatus, for example a packed column or plate column, mounted on the cleavage apparatus may be advantageous. This rectification apparatus is, as a rule, stabilized with polymerization inhibitors (eg. phenothiazine, hydroquinone monomethyl ether, etc.) during operation.

The advantages of the novel process are in particular that higher conversions are achievable therewith than by known processes. Another advantage is that no diluent is necessary. Moreover, smaller amounts of catalyst are required and there is less environmental pollution since smaller amounts of residue have to be disposed of.

The distillation conditions depend on the type of alcohol components used in the esterification. As a rule, a temperature of from 100° to 300° C. and a pressure from 1 to 50 mbar are envisaged. Any conventional distillation apparatus is suitable for the process. Since only a simple separation object is to be achieved, a simple splashguard is generally sufficient, ie. a column is usually not necessary.

The conditions for carrying out the novel process for the cleavage of the oxyesters which were distilled off from the bottom product are the following:

Catalyst: at least one acid selected from the group consisting of mineral acids, eg. sulfuric acid and phosphoric acid, and organic acids, such as alkanesulfonic or arylsulfonic acids, for example methanesulfonic acid or p-toluenesulfonic acid Amount of catalyst: 1–20, preferably 5–15, % by weight, based on the amount of the oxyester distillate Temperature: 150°–250° C., preferably 180°–230° C.

Pressure: preferably atmospheric pressure or reduced pressure (so that the cleavage products vaporize immediately)

Stripping gas, if required Amount: 10–100 l/h

Reaction time: 1–10 hours

Conversion: ≧90%

The reaction is carried out, for example, in such a way that the oxyester distillate to be cleaved and originating from the bottom product is fed continuously with the cleavage catalyst to the cleavage reactor. The reaction can also be carried out batchwise. Also possible is a semicontinuous reaction procedure in which the product to be cleaved is fed continuously to the cleavage reactor which contains the cleavage catalyst, and the remaining bottom product is removed batchwise from the cleavage reactor only after the end of the cleavage. The cleavage products are separated off continuously by distillation. As stated above, it may be advantageous to carry out the cleavage in the presence of a stripping gas (eg. air). The cleavage products are thus removed rapidly from the reaction mixture and the formation of undesirable byproducts is reduced. Preferably the cleavage products obtained are recycled directly to the esterification.

The applicability of the cleavage process described is not restricted to a special nature of the esterification process in which the byproducts obtained on the oxyesters, ie. the adducts I and II. As a rule, the esters are prepared by the conventional processes (cf. Ullmann's Encyclopedia of Industrial Chemistry, Vol. A1, 5th Ed., VCH, page 167 et seq.).

A typical example of the conditions under which the esterification can take place may be described briefly as follows:

Alcohol: (meth)acrylic acid 1:0.7–1.2 (molar)

Catalyst: Sulfuric acid or sulfonic acids

Amount of catalyst: 0.1–10% by weight (preferably 0.5–5% by weight), based on starting materials Stabilization: 200–2000 ppm of phenothiazine (based on the weight of the starting materials)

Reaction temperature: 80°–160° C., preferably 90°–130° C.

Reaction time: 1–10, preferably 1–6, hours

If required, an entraining agent (eg. cyclohexane or toluene) is used for removing the water formed in the esterification. The esterification can be carried out under atmospheric, superatmospheric or reduced pressure, both continuously and batchwise.

In the acid-catalyzed esterification of acrylic acid with alkanols, the bottom product resulting after the acidic esterification catalyst, the unconverted starting materials and the acrylate have been separated off generally has the following composition:

1–20% by weight of acrylate

50–80% by weight of alkoxypropionates (cf. formula I)

5–30% by weight of acyloxypropionates (cf. formula II)

Remainder: mainly stabilizers (phenothiazine) and polymers.

Further details and advantages of the novel process are stated in the Examples described below.

COMPARATIVE EXAMPLE

A circulation reactor (volume: 1 l) which consists of glass and is heated by means of a heating element was filled with 40 g of p-toluenesulfonic acid and 500 g of an esterification residue from the preparation of butyl acrylate, which residue had been freed from the acidic esterification catalyst. Below, butyl is n-butyl. The residue contained 10.1% by weight of butyl acrylate, 65.4% by weight of butoxyester I and 20.0% by weight of acyloxyester II ($R=C_4H_9$). The remainder consisted of polymers, oligomers and polymerization inhibitor (phenothiazine). The cleavage temperature was 195° C. and the working pressure was 1 atm.

Esterification residue was fed continuously to the cleavage reactor during the cleavage, with level control.

The cleavage products were removed in vapor form and condensed. An empty column (50 cm×2.8 cm) was present as a splashguard between reactor and condenser. 1589 g of esterification residue were fed to the cleavage in the course of 21.5 hours in this manner. According to the gas chromatographic analysis, the resulting condensate (1278 g) contained:

69.1% by weight of butyl acrylate
18.3% by weight of butanol
6.5% by weight of acrylic acid
7.0% by weight of olefins and ethers
3.5% by weight of butyl butoxypropionate Conversion: 84% by weight, based on oxyester.

The cleavage residue was viscous at room temperature and contained solids. Only after the addition of a conventional solvent was the residue pumpable.

The Examples which follow indicate the results obtained with the novel process. These Examples are divided into the process segments:

A—Distillation of the bottom liquid obtained in the esterification

B—Cleavage of the distillate formed in A

EXAMPLE 1

1A - Distillation

A distillation apparatus consisting of a round-bottomed flask (21), an attached column (50 cm×2.8 cm; 5 mm Raschig rings) and a condenser was filled with 1 l of a bottom liquid obtained in the preparation of butyl acrylate, containing no more acidic esterification catalyst and having the following composition:

10.1% by weight of butyl acrylate
65.4% by weight of butoxyester I (R=$C_4H_9$)
20.0% by weight of acyloxyester II (R=$C_4H_9$)
Remainder: mainly polymers and phenothiazine (polymerization inhibitor)

The distillation temperature was 145° C. and the pressure 30 mbar. The liquid level in the distillation flask was kept constant by continuous addition of the bottom liquid (300 g/h). 10% by weight of the amount of feed was removed from the distillation apparatus as bottom product of the distillation. According to the gas chromatographic analysis, the resulting distillate contained:

11.0% by weight of butyl acrylate
64.8% by weight of butoxyester I (R=$C_4H_9$)
20.5% by weight of acyloxyester II (R=$C_4H_9$)

Stabilization of the column with phenothiazine or another conventional stabilization was not necessary. The resulting bottom product of the distillation was still easy to handle (pumpable) at 25° C. and contained no solids.

1B - Cleavage

A circulation reactor (volume 1 l) consisting of glass and heated by means of a heating element was filled with 500 g of distillate from the distillation of the esterification residue (1A) and 40 g of p-toluenesulfonic acid. The cleavage temperature was 195° C. The operating pressure was 1 atm. The mixture to be cleaved was fed continuously to the cleavage reactor under level control. The cleavage products were removed in vapor form and condensed at the top of the column (50 cm×2.8 cm, empty) mounted on the cleavage reactor. 7401 g of mixture were fed into the cleavage over 119.5 hours, and 7080 g of cleavage products were condensed. According to the gas chromatographic analysis, the condensate contained 72.0% by weight of butyl acrylate
13.9% by weight of butanol
4.8% by weight of acrylic acid
1.4% by weight of dibutyl ether
6.6% by weight of butenes
0.2% by weight of butyl butoxypropionate Conversion: 96% by weight The bottom product of the cleavage was still easy to handle (pumpable) at 25° C. and contained no solids.

EXAMPLE 2

2A - Distillation

A distillation apparatus consisting of a round-bottomed flask (21), an attached column (30 cm×2.8 cm, 5 mm Raschig rings) and a condenser was filled with 1000 g of liquid bottom product which was obtained in the preparation of 2-ethylhexyl acrylate, contained no more acidic esterification catalyst and had the following composition:

65.0% by weight of alkoxyester I (R=$C_8H_{17}$)
5.5% by weight of acyloxyester II (R=$C_8H_{17}$)
2.1% by weight of 2-ethylhexyl acrylate
1.0% by weight of di-2-ethylhexyl ether
Remainder: Polymers, oligomers, polymerization inhibitor (phenothiazine)

The distillation was carried out at 1 mbar to a bottom temperature of 250° C. According to the gas chromatographic analysis, the distillate (763 g) contained:

89.5% by weight of alkoxyester I (R=$C_8H_{17}$)
5.2% by weight of acyloxyester II (R=$C_8H_{17}$)
3.5% by weight of 2-ethylhexyl acrylate
1.0% by weight of di-2-ethylhexyl ether The resulting bottom product of the distillation was still easy to handle (pumpable) at 25° C. and contained no solids.

2B - Cleavage

A cleavage reactor consisting of a 1 l stirred reactor, an attached column (30 cm×2.8 cm, 5 mm Raschig rings) and a condenser was filled with 500 g of distillate from the distillation (2A) and 10 g of p-toluenesulfonic acid. The cleavage was carried out at 180° C. and 50 mbar. The reaction time was 2 hours. According to the gas chromatographic analysis, the condensate (570 g) contained:

1.4% by weight of acrylic acid
16.2% by weight of 2-ethylhexanol
70.9% by weight of 2-ethylhexyl acrylate
3.7% by weight of di-2-ethylhexyl ether
6.1% by weight of octenes
1.8% by weight of alkoxyester I (R=$C_8H_{17}$)

Conversion: 95% by weight

The bottom product of the cleavage was easy to handle (pumpable) at 25° C. and contained no solids.

The above Examples of the novel process show that, on the one hand, considerably higher conversions are achievable by means of this process than by means of known processes and, on the other hand, that no diluents are required in order to remove the bottom product obtained in the cleavage.

We claim:

1. A process for esterifying (meth)acrylic acid with an alkanol in the presence of an esterification catalyst, in which unconverted starting compounds and the (meth)acrylate to be formed are separated off by distillation and an oxyester-containing bottom product is formed, wherein the bottom product is first separated off, the oxyesters contained therein are then separated off by distillation and the resulting distillate is cleaved in the presence of acids at elevated temperatures.

2. A process as claimed in claim 1, which is carried out in the presence of molecular oxygen.

3. A process as claimed in claim 1, wherein the distillate is cleaved at from 170° to 250° C., preferably from 180° to 230° C.

4. A process as claimed in claim 1, wherein the acid added to the distillate is one selected from the group consisting of mineral acids, such as sulfuric acid and phosphoric acid, and organic acids, such as alkanesulfonic and arylsulfonic acids, eg. methanesulfonic acid or p-toluenesulfonic acid.

5. A process as claimed in claim 4, wherein the amount of acid added is from 1 to 20, preferably from 5 to 15, % by weight, based on the distillate.

6. A process as claimed in claim 1, wherein the cleavage is carried out at reduced pressure (<1 atm).

7. A process as claimed in claim 1, wherein, in order to remove the cleavage products, a stripping gas is fed through the distillate to be cleaved.

8. A process as claimed in claim 7, wherein the stripping gas used is an oxygen-containing gas.

9. A process as claimed in claim 1, wherein the cleavage products obtained are recycled directly to the esterification.

10. A process as claimed in claim 1, wherein the distillate was obtained from the bottom product of the esterification with n-butanol or 2-ethylhexanol.

11. A process, comprising:
  esterifying (meth)acrylic acid with an alkanol in the presence of an esterification catalyst;
  distilling and separating the resulting (meth)acrylate and unconverted starting compounds from an oxyester-containing bottom product;
  distilling and separating the oxyesters from said oxyester-containing bottom product; and
  cleaving said oxyesters in the presence of at least one acid.

* * * * *